US006924416B2

(12) United States Patent
Guillen

(10) Patent No.: US 6,924,416 B2
(45) Date of Patent: Aug. 2, 2005

(54) TRAILING INTERSPECIFIC IMPATIENS

(75) Inventor: Mario Guillen, Cartago (CR)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 09/473,386

(22) Filed: Dec. 28, 1999

(65) Prior Publication Data

US 2002/0138883 A1 Sep. 26, 2002

(51) Int. Cl.$^7$ ............................ A01H 5/00; A01H 1/00; A01H 1/02
(52) U.S. Cl. ...................... 800/269; 800/323; 800/298; 800/260
(58) Field of Search ............................... 800/269, 323, 800/298, 260; Plt./318

(56) References Cited

U.S. PATENT DOCUMENTS

| | | | |
|---|---|---|---|
| PP4,720 P | | 5/1981 | Ryan |
| PP5,134 P | | 11/1983 | Mikkelsen |
| PP5,598 P | * | 12/1985 | Hope ......................... Plt./318 |
| PP5,698 P | * | 3/1986 | Hope ......................... Plt./318 |
| PP5,921 P | * | 3/1987 | Hope ......................... Plt./318 |
| PP6,729 P | | 4/1989 | Kientzler |
| PP6,732 P | | 4/1989 | Kientzler |
| PP7,098 P | | 1/1990 | Drewlow |
| PP10,495 P | | 7/1998 | Danziger |
| PP10,858 P | | 4/1999 | Kientzler |

OTHER PUBLICATIONS

The New Royal Horticultural Society Dictionary of Gardening, 1992. vol. 2, D to K, The Macmillan Press Limited, pp. 650.*

Fehr, Walter, Principles of Cultivar Development, 1987. McGraw–Hill, Inc., vol. 1, p. 96.*
Arisumi, Toru, Chromosome Numbers and Interspecific Hybrids Among New Guinea Impatiens Species, *The Journal of Heredity*, 77–79.
Arisumi, Toru, In Vito Culture of Embryos and Ovules of Certain Incompatible Selfs and Crosses among Impatiens Species, *J. Amer. Soc. Hort. Sci.*, 105(5)629–631, (1980).
Arisumi, Toru, Rescuing Abortive Impatiens Hybrids through Aseptic Culture of Ovules, *J. Amer. Soc. Hort. Sci.*, 110(2):273–276, (1985).
Arisumi, Toru, Cytology and Morphology of Ovule Culture–derived Interspecific Impatiens Hybrids, *J. Amer. Soc. Hort. Sci.*, 112(6):1026–1031, (1987).
New Guinea Impatiens, *A Ball Guide*, edited by W. Banner and M. Klopmeyer Ball Publishing (1995).
Strefeler, Mark, Genetics, *New Guinea Impatiens*,, Chapter 20, 227–247.
Hortus Third A Concise Dictionary of Plants Cultivated in the United States and Canada, *MacMillan Publishing Company* pp. 594–595, (1976).
Abstract, F1 Hybrid New Grinea Impatiens, *Ball Seed & Plant Catalog* 1999–2000, Ball Horticultural Company (1999), pp. 54–55.
Stephens, L.C., *Hereditas*, 251–255 (1998).

* cited by examiner

*Primary Examiner*—Andrew Wang
*Assistant Examiner*—June Hwu
(74) *Attorney, Agent, or Firm*—Wood, Phillips, Katz, Clark & Mortimer

(57) ABSTRACT

The present invention relates to an interspecific impatiens plant having a trailing habit. The plant of the present invention were developed as a result of a unique interspecific cross between *Impatiens flaccida* and *Impatiens Hawkeri*.

6 Claims, 3 Drawing Sheets

(3 of 3 Drawing Sheet(s) Filed in Color)

TRAILING INTERSPECIFIC IMPATIENS

FIELD OF INVENTION

The present invention relates to a novel trailing habit in interspecific impatiens plants. The trailing impatiens plants of the present invention were developed through a unique interspecific cross between *Impatiens flaccida* and *Impatiens Hawkeri*.

This invention also relates to interspecific impatiens seed, interspecific impatiens plants, interspecific impatiens varieties and interspecific impatiens hybrids containing this trailing trait.

In addition, the present invention also relates to methods for transferring the trailing habit to New Guinea impatiens varieties using *Impatiens flaccida* in breeding as either a female or male parent, in order to produce novel types and varieties of interspecific impatiens plants which exhibit this trailing habit. The present invention also relates to a $F_1$ hybrid or later generation interspecific impatiens plant grown from the interspecific hybrid seed produced by the aforementioned methods.

BACKGROUND OF INVENTION

The genus Impatiens is comprised of about 500 species of annual or perennial herbs or subshrubs. They are widely distributed particularly in the tropics and subtropics of Asia and Africa (*Hortus Third A Concise Dictionary of Plants Cultivated in the United States and Canada*, MacMillan Publishing Company (1976)).

A species of particular commercial interest is *Impatiens Hawkeri*, commonly referred to as New Guinea impatiens. New Guinea impatiens have foliage and floral characteristics that are desirable for bedding and pot-plant use. Impatiens plants reported to be native to New Guinea were classified in 1886 as *Impatiens Hawkeri* (*New Guinea Impatiens, A Ball Guide*, edited by W. Banner and M. Klopmeyer, Ball Publishing (1995)). Occasionally, these early specimens were referred to as *Impatiens herzogii*. Id. In the early 1900's, botanists from Germany, England and the Netherlands explored parts of the Sundra Islands, and by 1915, nine New Guinea impatiens species were identified from this area: *I. dahlii, I. herzogii, I. laxterbachii, I. linearifolia, I. mooreana, I. polyphylla, I. rodatzii, I. schlechteri,* and *I. trichura*. Id. Taxonomically, the collections were confusing and were considered to be habitat variations of *I. herzogii* rather than new species by Von R. Schlecter. Id. In the most recent taxonomic classification, Grey-Wilson proposed that New Guinea impatiens belong to one highly variable species, *I. Hawkeri*, in which 15 groups were identified based on geographic location. Id.

Although diverse phenotypically, typically members of New Guinea impatiens are fertile when crossed with each other or when selfed and generally have a 2n chromosome number of 32 (T. Arisumi, *J. Hered.*, 64:77–79 (1973)). Breeding programs initiated in the early 1970's have led to the development of New Guinea impatiens cultivars that are adapted to a variety of light conditions, and have large flowers of a wide variety of colors including white, pink, red, orange, as well as biocolors (*New Guinea Impatiens, A Ball Guide*, edited by W. Banner and M. Klopmeyer, Ball Publishing (1995)). Foliage types include slightly rounded to lanceolate with smooth to serrated edges having colors ranging from green to burgundy and variegated. Id. Plant habits are typically mounded to spreading (Plant U.S. Pat. No. 5,921; Plant U.S. Pat. No. 4720; Plant U.S. Pat. No. 10,858). One cultivar 'Radiance' is described as having stems that are "slightly trailing" (Plant U.S. Pat. No. 7,098).

Interspecific crosses using *Impatiens platypetala* and *Impatiens aurantiaca*, two species closely related to *Impatiens Hawkeri*, have been used in New Guinea impatiens cultivar improvement, but offspring of these crosses are often sterile (*New Guinea Impatiens, A Ball Guide*, edited by W. Banner and M. Klopmeyer, Ball Publishing (1995)). Arisumi has successfully used ovule culture to recover interspecific hybrids of New Guinea impatiens, *I. Hawkeri*, crossed with *I. auricoma, I. niamniamensis, I. uguenensis*, and *I. Wallerana* (*I. sultani* in his publication) (T. Arisumi, *J. Amer. Soc. Hort. Sci.* 112(6): 1026–1031 (1987)).

*Impatiens flaccida alba*, a species noted for drought tolerance, has been used in interspecific crosses. Using ovule culture, hybrid seedlings were recovered from interspecific crosses of *I. flaccida alba x I. repens* and *I. uguenensis x I. flaccida alba*; however, no seedlings were recovered from crosses of *I. flaccida alba x I. herzogii, I. flaccida alba x I. epiphytica*, or *I. flaccida alba x I. hookeriana* (T. Arisumi, *J. Amer. Soc. Hort. Sci.* 105(5):629–631 (1980)). An additional study confirmed the previously reported *I. flaccida alba x I. repens* and *I. uguenesis x I. flaccida alba* successes, while no seedlings were recovered from a cross between *I. flaccida alba x 'Pele'* (A New Guinea impatiens cultivar) (T. Arisumi, *J. Amer. Soc. Hort. Sci.* 110(2):273–276 (1985)). Interspecific hybrids were also recovered from a cross between *I. flaccida x I. Wallerana* 'Elfin White' (*I. sultani* in his publication) (T. Arisumi, *J. Amer. Soc. Hort. Sci.* 112(6): 1026–1031 (1987)).

SUMMARY OF INVENTION

The present invention relates to interspecific impatiens plants having a novel trailing habit. The interspecific impatiens plants of the present invention possess a trailing habit and have pedigrees which include 2245B, 2257B or derivatives thereof.

The present invention also relates to seed, pollen, cuttings and ovules of the trailing interspecific impatiens plants of the present invention. Moreover, the present invention also relates to a tissue culture comprising regenerable cells of the trailing interspecific impatiens plants of the present invention.

Additionally, the present invention relates to interspecific impatiens seed which contain the trailing trait. The seed of the present invention have pedigrees which include 2245B, 2257B or derivatives thereof The present invention also relates to a trailing interspecific impatiens plant produced by growing the seed of the present invention.

The present invention also relates to a method for transferring the trailing trait from *Impatiens flaccida* into *Impatiens Hawkeri*. The method involves crossing pollen from a first parent impatiens plant to a second parent impatiens plant and harvesting the resultant first generation ($F_1$) hybrid impatiens seed. One of the parent impatiens plants used in said method must be an *Impatiens flaccida*. Additionally, the present invention relates to a first generation ($F_1$) hybrid plant produced by growing the hybrid seed produced by said method.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

DETAILED DESCRIPTION OF THE INVENTION

Figure 1:
FIG. 1 shows a photograph of an *Impatiens flaccida* x *Impatiens Hawkeri* hybrid named 2245B of the present invention that is approximately 12 weeks old.
Figure 2:
FIG. 2 shows a photograph of hybrid 2245B that is approximately 20 weeks old.
Figure 3:
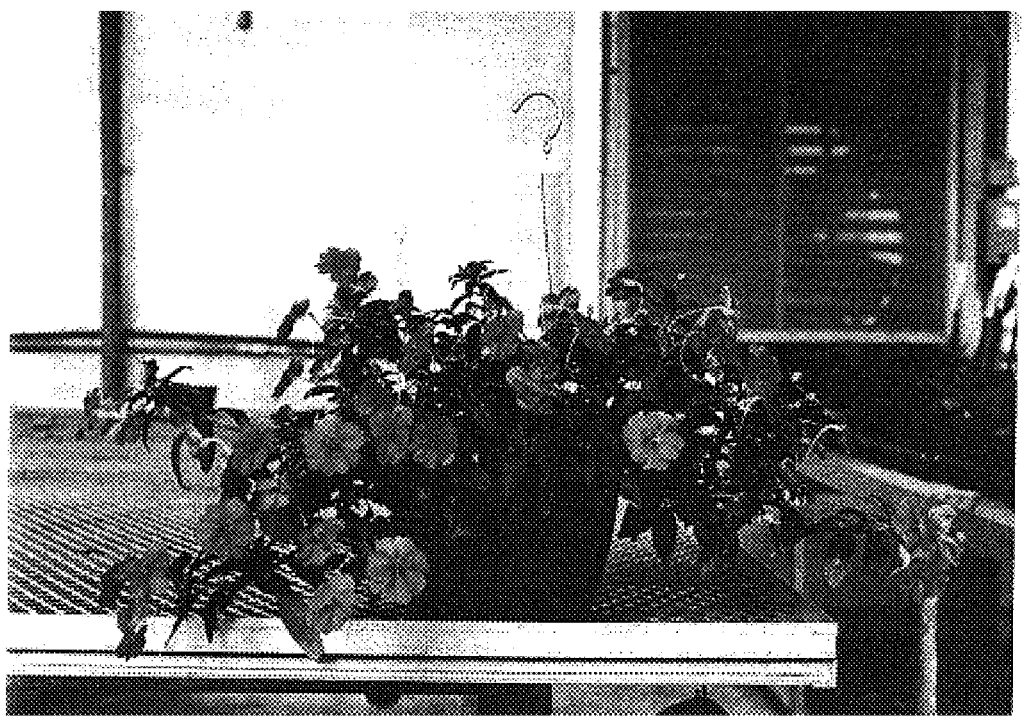
FIG. 3 shows a photograph of an *Impatiens flaccida* x *Impatiens Hawkeri* hybrid named 2257B of the present invention that is approximately 12 weeks old.

The interspecific impatiens plants of the present invention exhibit an unique trailing habit. This trailing habit was developed through a unique interspecific cross between *Impatiens flaccida* and *Impatiens Hawkeri*.

As used herein, the term "trailing" means a plant habit wherein lateral branches of the plant extend over the container and grow toward the ground.

The previously unknown trailing interspecific impatiens plants of the present invention were discovered as a result of a breeding and research efforts which were conducted in Linda Vista, Costa Rica. In 1996, a cross was made using a proprietary *Impatiens flaccida* Linda Vista as the female parent, grown from seed, a sample of which is deposited under ATCC Accession Number PTA-1069. This selection exhibited very vigorous growth, small lavender flowers, good pollen and seed yield, and is early to flower with a spreading, loose habit. The male parent was a bulk of *Impatiens Hawkeri* pollen collected from the Java Series $F_1$ hybrid New Guinea impatiens (developed by and commercially available from Pan American Seed Company, 622 Town Road. West Chicago, Ill. 60185). The plants in this series have medium vigor with a bushy, well-branched habit. They have good pollen and seed yield, and are early to flower with abundant flower production. Pollen was collected from several plants having a variety of flower colors, and may have included orange, red, salmon, red/salmon bicolor, rose/lilac bicolor, lavender, cherry red and white. The bulked pollen was transferred to the female parent and the resulting $F_1$ seed was collected and germinated. In 1997, from the flowering progeny, plants identified as 2245B and 2257B were selected. The $F_1$ generation yielded a variety of flower colors including lilac, cherry red, and purple. Foliage colors included green to dark green. The majority of the $F_1$ plants were sterile and it was not possible to recover seed from self pollination or backcrossing.

Methods for overcoming interspecific hybrid sterility barriers are known in the art and include, but are not limited to, colchicine treatments, random assortive mating and naturally developing pollen fertility.

The trailing interspecific impatiens plants of the present invention are genetically stable and can be stably reproduced by means of asexual propagation. Cuttings for asexual propagation can be taken at any time of the year and no special hormones or soil mixtures are required. It is expected that any trailing interspecific impatiens can be produced commercially through asexual propagation.

Using the methods described herein, it is expected that the trailing trait from *Impatiens flaccida* can be bred into diverse New Guinea (*Impatiens Hawkeri*) impatiens backgrounds, including those having many different flower colors, as well as bicolor flowers. Additionally, the trailing habit can be incorporated into New Guinea impatiens having solid green foliage, green and yellow variegated foliage, dark green foliage, dark purplish leaves, dark purplish and cream variegated foliage, etc.

The following examples are set forth as representations of specific and preferred embodiments of the present invention. These examples are not to be construed as limiting the scope of the invention in any manner. It should be understood that many variations and modifications can be made while remaining within the spirit and scope of the invention.

EXAMPLE 1

Description of *Impatiens flaccida* x *Impatiens Hawkeri* hybrid named 2245B

The color chart used in the identification of colors described herein is the R.H.S. Colour Chart of The Royal Horticultural Society, London, England. The color values were determined on Oct. 8, 1999 in West Chicago, Ill. The readings were taken between 1:00 and 1:45 p.m. under approximately 2500 footcandles of light.

The plants were produced from cuttings taken from stock plants and were grown under greenhouse conditions comparable to those used in commercial practice while utilizing a soilless growth medium and maintaining temperatures of approximately 72° F. during the day and approximately 65° F. during the night.

| | |
|---|---|
| Propagation | |
| Type cutting | Terminal tip |
| Time to initiate roots | Approximately 14–21 days with the shorter times generally being experienced in the summer and the longer times in the winter |
| Rooting habit | Fibrous, branching |
| Plant Description | |
| General appearance and form | Trailing |
| Crop time | A finished flowering plant is produced 8 to 10 weeks after planting rooted cuttings |
| Branching habit | Freely basal branching without pinching or growth regulators |
| Total number of branches | Approximately 55 equal to or longer than 5 mm |
| Branch length | Approximately 19.3 cm |
| Branch diameter | Approximately 8 mm |
| Internode length | Approximately 4.5 cm |
| Stem color | Yellow-Green Group 144D overlaid with Greyed-Purple Group 183B at nodes |
| Height of foliage | A mature plant commonly measures approximately 17 cm above a 20 cm pot |
| Length of foliage | Approximately 17 cm below top of a 20 cm pot |
| Area of spread | Approximately 45 cm with three plants per 20 cm pot |
| Foliage Description | |
| Form | Ovate with acuminate apex and cuneate base |
| Margin | Serrate, ciliate |
| Arrangement | Opposite |
| Venation pattern | Arcuate |
| Surface | Smooth |
| Color of mature foliage-upper surface | Between Green Group 137A and Green Group 146A with veins of Yellow-Green Group 145C |
| Color of mature foliage-lower surface | Closest to Green Group 138B with veins of Yellow-Green Group 144C |
| Size | Approximately 6.3 cm in length; approximately 2.4 cm in width |
| Petiole length | 1.1 cm |
| Petiole diameter | 2 mm |
| Petiole color | Yellow-Green Group 145C with faint overlay of Red Group 52B at base |
| Flower Description | |
| Flowering habit | Freely flowering under outdoor growing conditions with substantially continuous blooming from spring until fall |
| Flowers borne | Above foliage arising from leaf axils |
| Peduncle length | 4.9 cm |

-continued

| | |
|---|---|
| Peduncle color | Yellow-Green Group 145C with slight overlay of Red-Group 52B on lower third. |
| Flower form | Single |
| Quantity of flowers | Approximately 26 per plant |
| Flower size | Approximately 4.6 cm in diameter |
| Number of petals | Five |
| Petal texture | Iridescent |
| Petal shape | Obovate |
| Petal margin | Entire |
| Petal apex | Superior petal is flat; other four petals are emarginate |
| Petal base | Superior petal has very broad base; other petals have narrow, pointed base |
| Petal length | Superior petal is 1.8 cm; other four petals are 2.6 cm |
| Petal width | Superior petal is 2.4 cm; other four petals are 2.1 cm |
| Flower color | The upper surface of all petals is between Red-Purple Group 64A and Red-Purple Group 74A. The two lateral petals have bases of Red-Purple Group 72B; and the lowest two petals have bases of Red-Purple Group 72B with areas of Red-Purple Group 60A just above the bases forming an "eye". The lower surface of all petals is closest to Red-Purple Group 67A. |
| Flower bud shape | Ovate |
| Flower bud length | 1.7 cm |
| Flower bud diameter | 8.3 mm |
| Flower bud color | Closest to Red-Purple Group 71B |
| Sepals | Three sepals plus two rudimentary sepals are fused into the under surface of the superior petal. A spur originating from the base of the inferior sepal is approximately 5.5 cm in length on fully opened flowers. The spur color is Red-Purple Group 58A with Yellow-Green Group 144C at tip. |
| Reproductive organs | The stamens and anthers are fused together forming one organ that surrounds the pistil. The pistil is approximately 5 mm long, the stigma color is Yellow-Green Group 144D, and the ovary color is Yellow-Green Group 144A. Generally, the anthers shed pollen prior to the stigma becoming receptive. The pollen color is Yellow Group 13D. |

EXAMPLE 2

Description of *Impatiens flaccida x Impatiens Hawkeri* hybrid named 2257B

The color chart used in the identification of colors described herein is the R.H.S. Colour Chart of The Royal Horticultural Society, London, England. The color values were determined on Oct. 8, 1999 in West Chicago, Ill. The readings were taken between 1:00 and 1:45 p.m. under approximately 2500 footcandles of light.

The plants were produced from cuttings taken from stock plants and were grown under greenhouse conditions comparable to those used in commercial practice while utilizing a soilless growth medium and maintaining temperatures of approximately 72° F. during the day and approximately 65° F. during the night.

| | |
|---|---|
| Propagation | |
| Type cutting | Terminal tip |
| Time to initiate roots | Approximately 14–21 days with the shorter times generally being experienced in the summer and the longer times in the winter |
| Rooting habit | Fibrous, branching |
| Plant Description | |
| General appearance and form | Medium trailing |
| Crop time | A finished flowering plant is produced in 8 to 10 weeks after planting rooted cuttings |
| Branching habit | Freely basal branching without pinching or growth regulators |
| Total number of branches | Approximately 51 equal to or longer than 5 mm |
| Branch length | Approximately 21.3 cm |
| Branch diameter | Approximately 7 mm |
| Internode length | Approximately 5.1 cm |
| Stem color | Greyed-Purple Group 184A at base and above each node; Yellow-Green Group 144A just below each node |
| Height of foliage | A mature plant commonly measures approximately 19 cm above a 20 cm pot |
| Length of foliage | Approximately 15 cm below top of a 20 cm pot |
| Area of spread | Approximately 46 cm with three plants per 20 cm pot |
| Foliage Description | |
| Form | Lanceolate with acuminate apex and cuneate base |
| Margin | Serrate, ciliate |
| Arrangement | Whorles of three |
| Venation pattern | Arcuate |
| Surface | Smooth |
| Color of mature foliage-upper surface | Between Green Group 137A and Green Group 146A with veins of Yellow-Green Group 145C |
| Color of mature foliage-lower surface | Closest to Green Group 138B with veins of Yellow-Green Group 144C |
| Size | Approximately 6.3 cm in length; approximately 1.9cm in width |
| Petiole length | 9 mm |
| Petiole diameter | 2 mm |
| Petiole color | Yellow-Green Group 145C with faint overlay of Red Group 52B at base |
| Flower Description | |
| Flowering habit | Freely flowering under outdoor growing conditions with substantially continuous blooming from spring until fall |
| Flowers borne | Above foliage arising from leaf axils |
| Peduncle length | 5.4 cm |
| Peduncle color | Yellow-Green Group 145C with slight overlay of Red-Purple Group 60B |
| Flower form | Single |
| Quantity of flowers | Approximately 23 per plant |
| Flower size | Approximately 4.4 cm in diameter |
| Number of petals | Five |
| Petal texture | Iridescent |
| Petal shape | Obovate |
| Petal margin | Mostly entire with some incisions |
| Petal apex | Superior petal has rounded tip; other four petals are emarginate |
| Petal base | Superior petal has very broad base; other petals have narrow, pointed base |
| Petal length | Superior petal is 1.7 cm; other four petals are 2.3 cm |
| Petal width | Superior petal is 2.5 cm; other four petals are 2.1 cm |
| Flower color | The upper surface of the superior petal is between Purple-Violet Group 81C and Purple-Violet Group 81D. The two lateral petals are between Purple- Violet Group 81B and Purple-Violet Group 81C; and the lowest two petals are closest to Purple- Violet Group 81C with areas of Red-Purple Group 60A just above the bases forming an "eye". Lower surface of all petals is Violet Group 84A with midvein of Violet Group 84B. |
| Flower bud shape | Ovate |
| Flower bud length | 1.9 cm |
| Flower bud diameter | 1.2 cm |
| Flower bud color | Violet Group 84B |
| Sepals | Three sepals plus two rudimentary sepals are fused into the under surface of the superior petal. |

| | |
|---|---|
| Reproductive organs | A spur originating from the base of the inferior sepal is approximately 4.4 cm in length on fully opened flowers. The spur color is Red Group 49D at proximal end; Red Group 54C in the middle three- quarters; Yellow-Green Group 144C at tip. The stamens and anthers are fused together forming one organ that surrounds the pistil. The pistil is approximately 5 mm long, the stigma color is Yellow-Green Group 144C, and the ovary color is Yellow-Green Group 144A. Generally, the anthers shed pollen prior to the stigma becoming receptive. The pollen color is Yellow Group 13D. |

DEPOSIT INFORMATION

Two thousand five hundred (2500) seeds of *Impatiens flaccida* have been placed on deposit with the American Type Culture Collection (ATCO), 10801 University Blvd., Manassas, Va. 20110-2209 under Deposit Accession Number. PTA-1069 on Dec. 15, 1999. This deposit was made in compliance with the Budapest Treaty requirements that the duration of the deposit should be for thirty (30) years from the date of the deposit or for five (5) years after the last request for the deposit at the depository or for the enforceable life of a U.S. Patent that matures from this application, whichever is longer. These impatiens seeds will be replenished should it become non-viable at the depository.

The present invention is illustrated by way of the foregoing description and examples. The foregoing description is intended as a non-limiting illustration, since many variations will become apparent to those skilled in the art in view thereof It is intended that all such variations within the scope and spirit of the appended claims be embraced thereby.

Changes can be made to the composition, operation and arrangement of the method of the present invention described herein without departing from the concept and scope of the invention as defined in the following claims.

What is claimed is:

1. A method of producing an interspecific impatiens plant, the method comprising the steps of:
   a. crossing a *Impatiens flaccida* plant grown from seed, a sample of which is deposited under ATCC Accession Number PTA-1069, with a *Impatiens Hawkeri* plant;
   b. recovering the resultant $F_1$ hybrid interspecific impatiens seed;
   c. planting the resultant $F_1$ hybrid interspecific impatiens seed and growing into plants; and
   d. selecting resultant interspecific impatiens plant from step (c) having a trailing habit.

2. The method of claim 1, further comprising the step of taking a cutting of said selected trailing interspecific impatiens plant.

3. The method of claim 1 wherein the *Impatiens flaccida* plant is the male plant.

4. The method of claim 1 wherein the *Impatiens flaccida* plant is the female plant.

5. The method of claim 1 wherein the *Impatiens Hawkeri* plant is the male plant.

6. The method of claim 1 wherein the *Impatiens Hawkeri* plant is the female plant.

* * * * *